US00PP36984P2

(12) United States Plant Patent
Bagdasarian et al.

(10) Patent No.: US PP36,984 P2
(45) Date of Patent: Sep. 30, 2025

(54) STRAWBERRY PLANT NAMED 'GF Belle'

(50) Latin Name: ***Fragaria* x *ananassa***
Varietal Denomination: GF Belle

(71) Applicant: GoodFarms Genetics, LLC, San Diego, CA (US)

(72) Inventors: Jimmy Haig Bagdasarian, Santa Cruz, CA (US); Travis Stegmeir, Salinas, CA (US)

(73) Assignee: GoodFarms Genetics, LLC, San Diego, CA (US)

( * ) Notice: Subject to any disclaimer, the term of this patent is extended or adjusted under 35 U.S.C. 154(b) by 0 days.

(21) Appl. No.: 18/885,564

(22) Filed: Sep. 14, 2024

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./208, 209
See application file for complete search history.

(56) References Cited

U.S. PATENT DOCUMENTS

| | | | | |
|---|---|---|---|---|
| PP22,472 | P3 | 1/2012 | Bagdasarian | |
| PP26,974 | P3 | 7/2016 | Bagdasarian | |
| PP27,034 | P3 | 8/2016 | Bagdasarian | |
| PP27,190 | P3 | 9/2016 | Bagdasarian | |
| PP30,326 | P2 | 4/2019 | Bagdasarian | |
| PP30,426 | P2 | 4/2019 | Bagdasarian | |
| PP30,427 | P2 | 4/2019 | Bagdasarian | |
| PP33,284 | P2 | 7/2021 | Bagdasarian | |
| PP34,190 | P2 * | 5/2022 | Bagdasarian | A01H 6/7409 Plt./209 |
| PP34,367 | P3 * | 6/2022 | Hoekstra | A01H 6/32 Plt./382 |
| PP34,637 | P2 | 10/2022 | Bagdasarian | |

* cited by examiner

*Primary Examiner* — Susan McCormick Ewoldt
(74) *Attorney, Agent, or Firm* — Phase M Legal

(57) ABSTRACT

A new and distinct variety of strawberry plant named 'GF Belle' is described here. This new short-day strawberry variety is characterized by moderate vigor plants producing attractive conical fruit, which has a great, sweet strawberry flavor, and a desirable glossy light red exterior color. The variety is fully remontant in cool coastal areas of California, producing high quality fruit all season long. This variety also has a very open canopy, which allows ease of picking and spraying.

7 Drawing Sheets

Latin name of the genus and species of the plant claimed: Botanical classification: *Fragaria* x *ananassa.*

Variety denomination: The new strawberry denomination is 'GF Belle'.

BACKGROUND OF THE INVENTION

The present invention relates to a new and distinct variety of strawberry named 'GF Belle'. This new short-day strawberry variety is the result of a controlled cross in an ongoing breeding program made in 2017. The controlled cross, conducted in an ongoing breeding program, which resulted in the 'GF Belle' variety was between a strawberry variety designated 'Sweet Ann', (U.S. Plant Pat. No. 22,472), and a strawberry variety designated '001R11', (unpatented).

The controlled cross was carried out in a breeding program in Redding, California, USA. Pollen taken from the field of a '001R11' plant pollinated a female 'Sweet Ann' plant in a greenhouse. The flowers were emasculated to remove all pollen sources, and so that no other pollen could contaminate the procedure.

Strawberries developed, were harvested and the seeds resulting from this cross were extracted and germinated in a greenhouse in Redding, California, USA. The resulting seedlings were transplanted to Shastina, California in 2018, grown for an additional period and allowed to propagate asexually via stolons. Plants were then harvested and planted in breeding test plots in early to mid-October in:

Oxnard, California (Ventura County); and slightly later in Moss Landing, California (Monterey County). The selection of the new variety was first made in Oxnard, California, and designated '122X08' in 2018. This selection was later named 'GF Belle'. The new variety was further propagated asexually by stolons in breeding plots in: Macdoel, California (Siskiyou County); and Manteca, California (San Joaquin County).

The new variety has also been "meristemed." Small pieces of plant material (approximately 0.5 mm in diameter), consisting of the undifferentiated meristem tissue and one or two leaf primordia, were removed from the buds on crowns of young daughter plants, then placed on nutrient medium, and new plants were grown from them. Planting stock from the "meristemed" plants are growing in a screenhouse located in Redding, California.

The propagules of 'GF Belle' are identical to the original plant in all distinguishing characteristics: accordingly, the propagation has demonstrated that the traits disclosed herein remain fixed and true to type through successive generations of asexual reproduction.

COMPARISON TO PARENT VARIETIES

'GF Belle' produces very high quality, large, firm berries, which are attractive, and which have great flavor. The primary market for the 'GF Belle' variety is for fresh market sales of the fruit. The berries produced by the 'GF Belle' variety are relatively early fruiting, enabling growers to capture early market windows. The open canopy of 'GF Belle' also allows for more airflow, and more visible fruit for better spray coverage and ease of picking.

The female parent, 'Sweet Ann', is a day neutral (DN) variety characterized as a vigorous plant which produces large to very large, conical fruit. The fruit has an exceptional flavor, and 'Sweet Ann' has an open plant architecture as does 'GF Belle'. The male pollen parent, '001R11', is a short-day plant, characterized by its large, firm, conical fruit which has a dark red exterior and interior color. Plants of '001R11' are high vigor, with moderately dense foliage, and are mid-season producing.

SUMMARY OF THE INVENTION

'GF Belle' is a short-day variety exhibiting the following combination of characteristics, which have been observed repeatedly, and which distinguish this strawberry plant as a new and distinct variety:

1. The variety produces large sized fruit;
2. The fruit is well shaped conical;
3. The fruit is attractive, having a glossy red exterior and interior;
4. The fruit is sweet tasting, with great flavor;
5. The variety produces a high volume of marketable fruit;
6. The plants of the variety maintain an open architecture; and,
7. The variety is fully remontant in a cool, coastal environment.

'GF Belle' fruit demonstrates characteristics and qualities that are desired by fresh market strawberry sales companies. The moderate red color is preferred by many shippers of fresh strawberries, as darker berries are often viewed as overripe by buyers, than are lighter colored berries. 'GF Belle' is also a firm berry, which should lend well to a fresh market where shipping can be a major factor. The vigor is moderate, and the density of 'GF Belle' plants are more open, with flowers that extend slightly over the canopy, allowing for adequate pollination. Fruit is easily seen and accessible on the shoulders of the beds allowing for ease of picking. This moderate vigor and open canopy hold an advantage over dense canopies in that spray coverage is allowed to penetrate more efficiently over denser varieties, and berries are often able to dry faster after rain events.

BRIEF DESCRIPTION OF THE FIGURES

The accompanying color photographs, identified as FIGS. 1 through 7, show the appearance of typical specimens of the new strawberry variety, initially designated '122X08', and now named 'GF Belle'. These Figures depict the colors, as true as it is reasonably possible given differences in color illustrations of this character. Accordingly, color in the photographs May differ slightly from the colors discussed in the botanical description. The photographs of the depicted plant, plant parts, and fruit of 'GF Belle' in FIGS. 1 through 6 were taken in August 2023. The photograph in FIG. 7 was taken in August 2024.

DETAILED BOTANICAL DESCRIPTION OF THE PLANT

Figure 1:
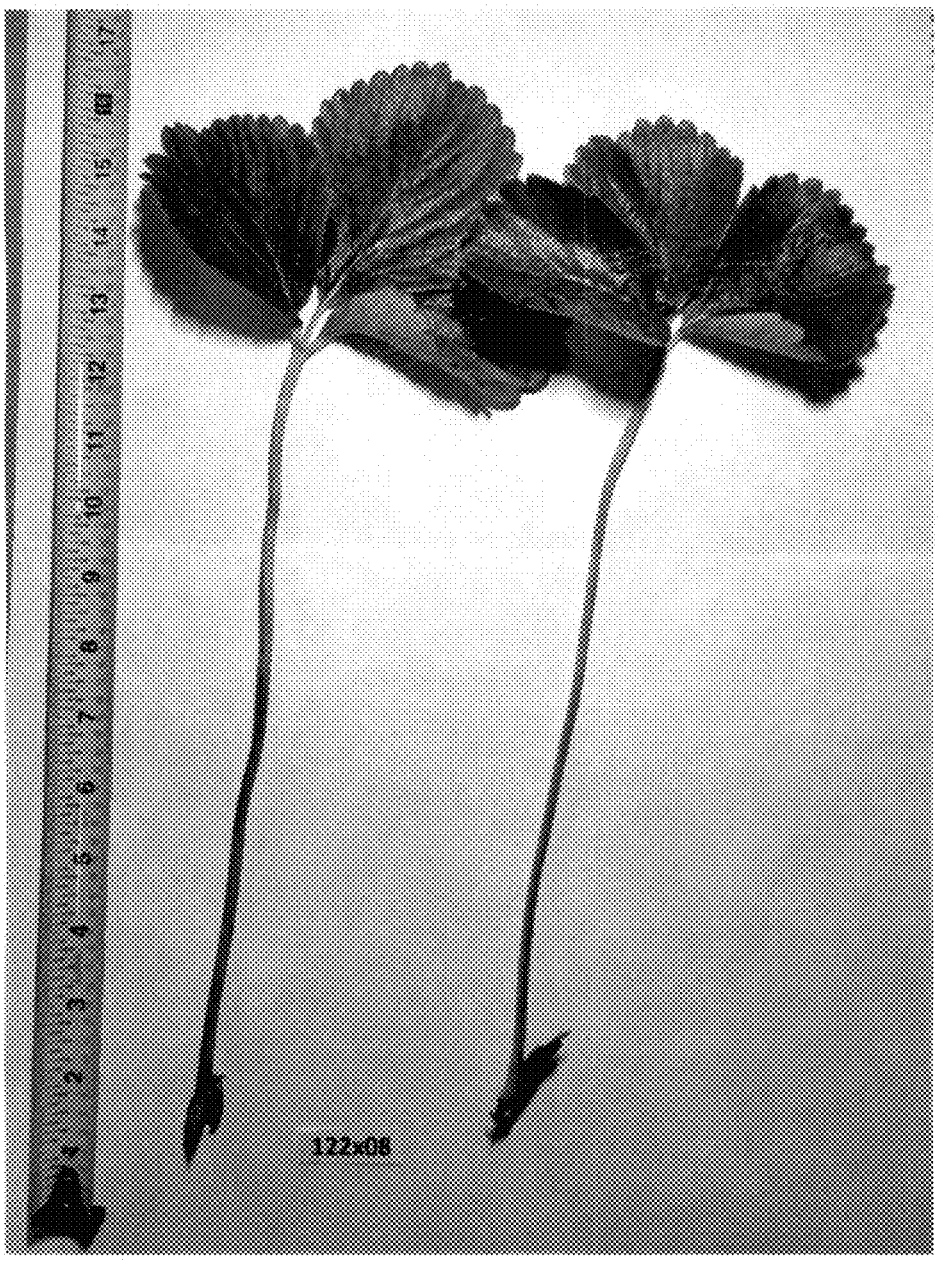
FIG. 1 shows typical leaf and petiole structure at mid-season.
Figure 2:
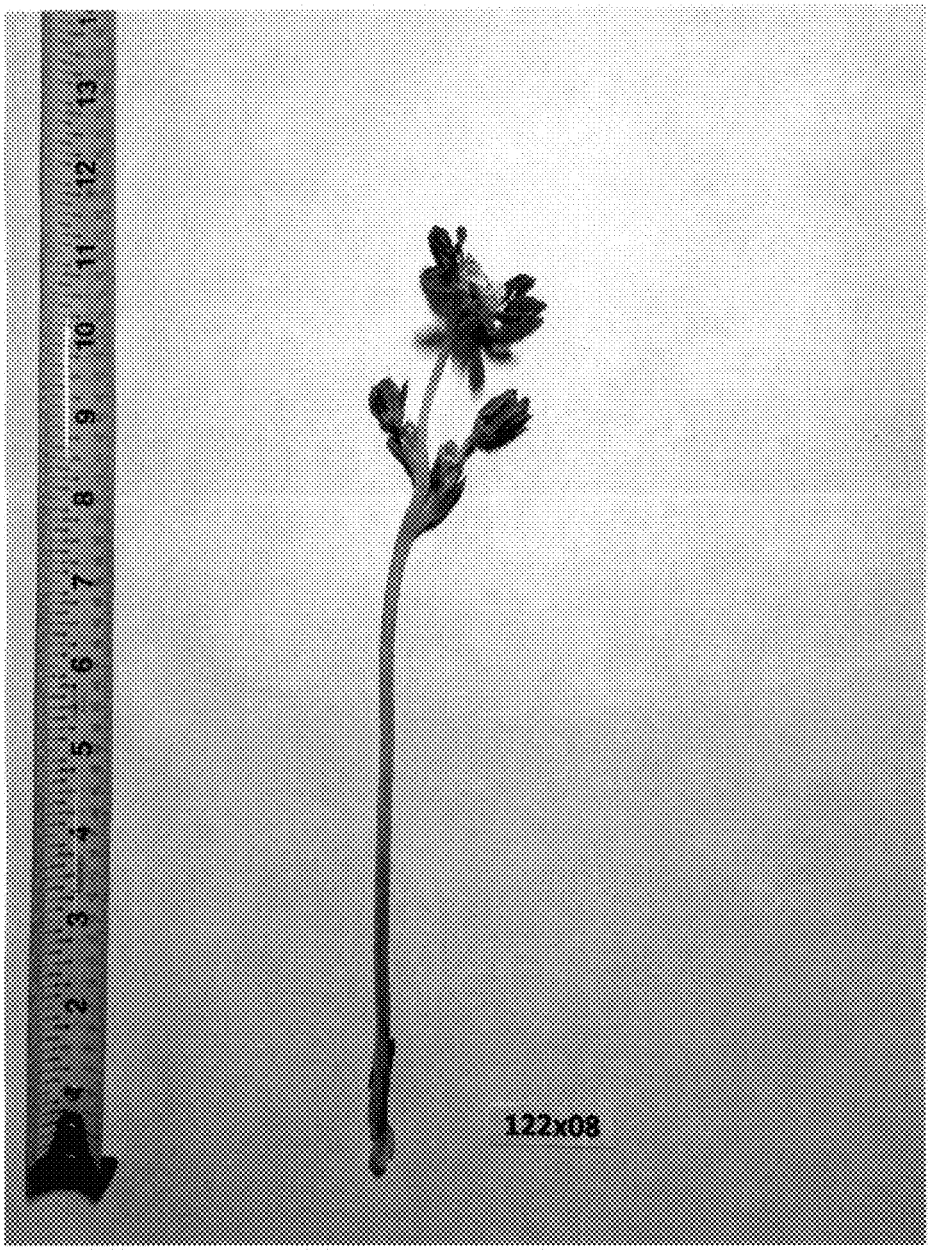
FIG. 2 shows an inflorescence at mid-season.
Figure 3:
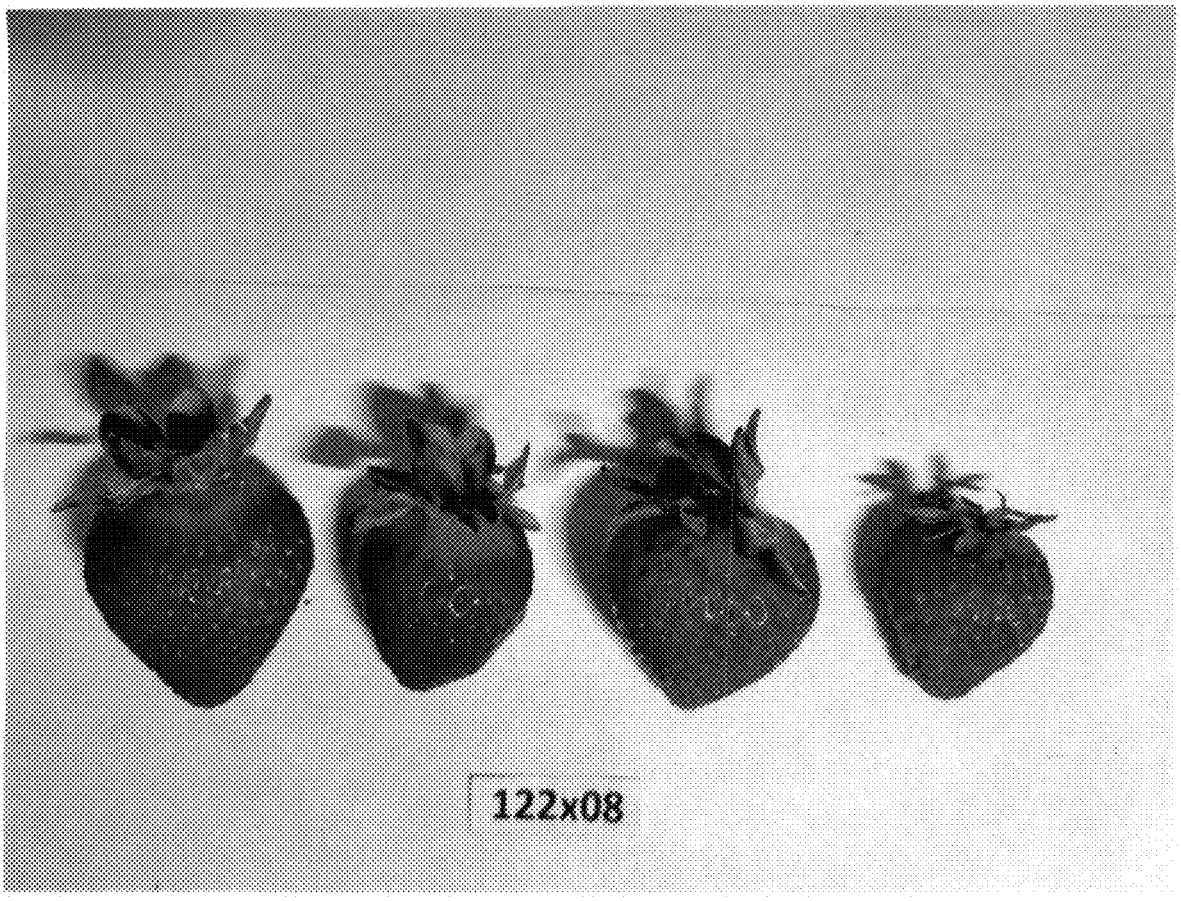
FIG. 3 shows a selection of typical mid-season fruit.
Figure 4:
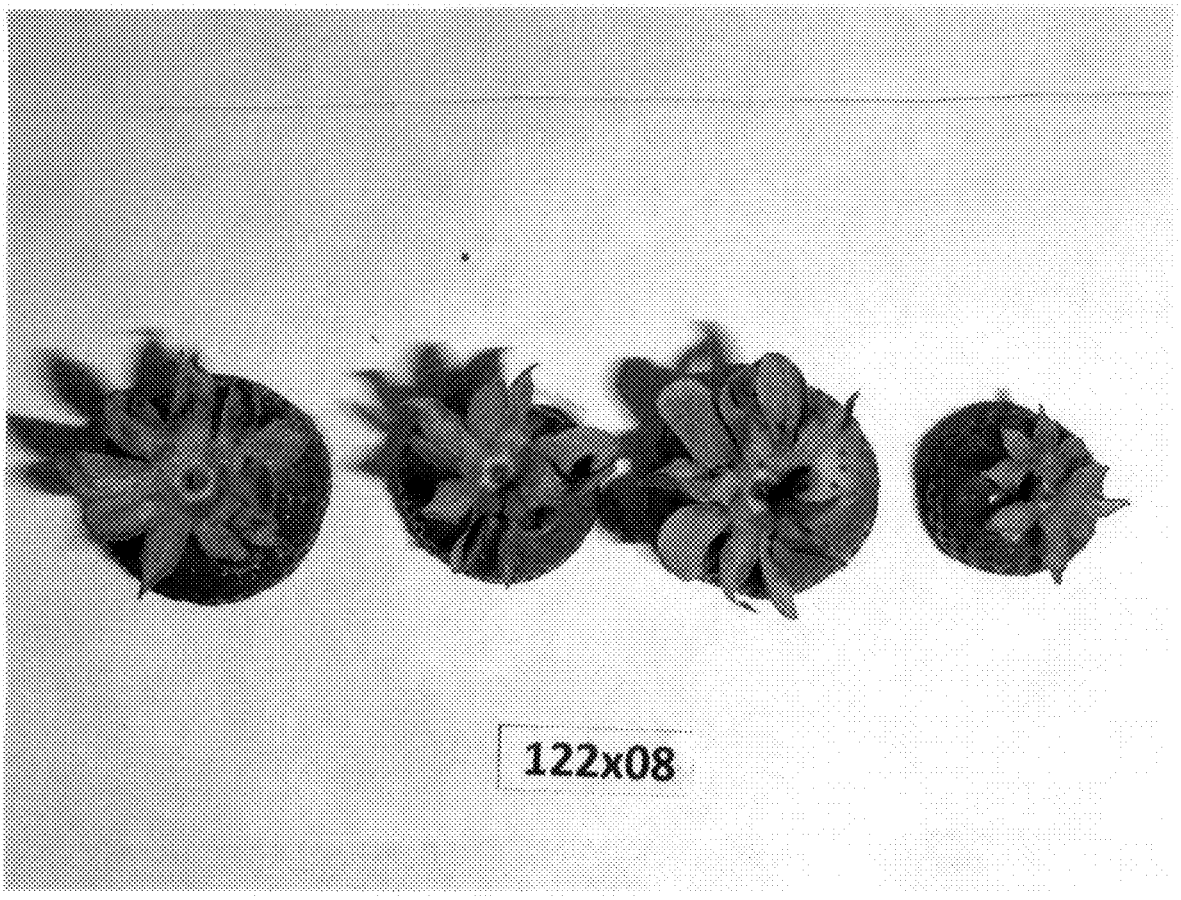
FIG. 4 shows typical calyx position over the berry of 'GF Belle'.
Figure 5:
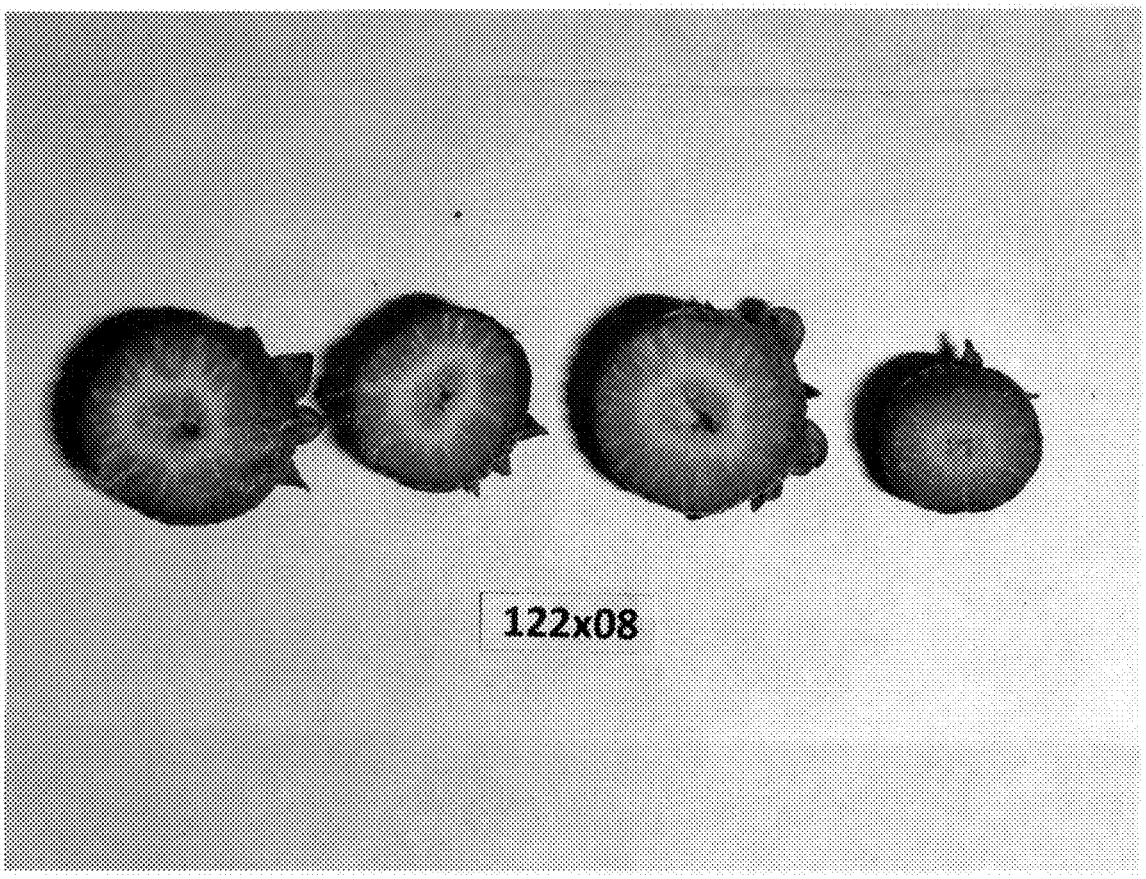
FIG. 5 shows a cross-section of typical fruit internal coloration and core size.
Figure 6:
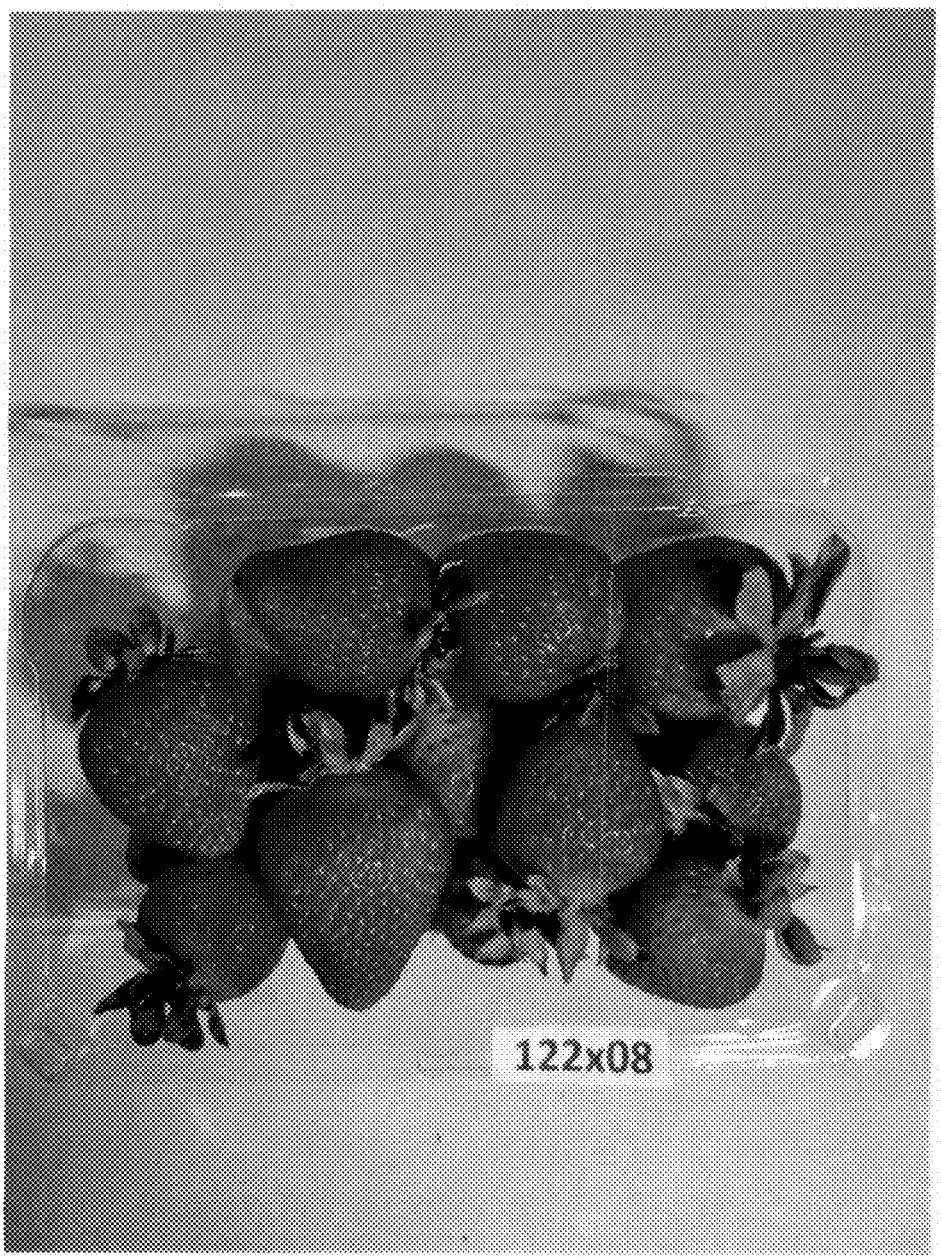
FIG. 6 shows a container of freshly picked fruit.
Figure 7:
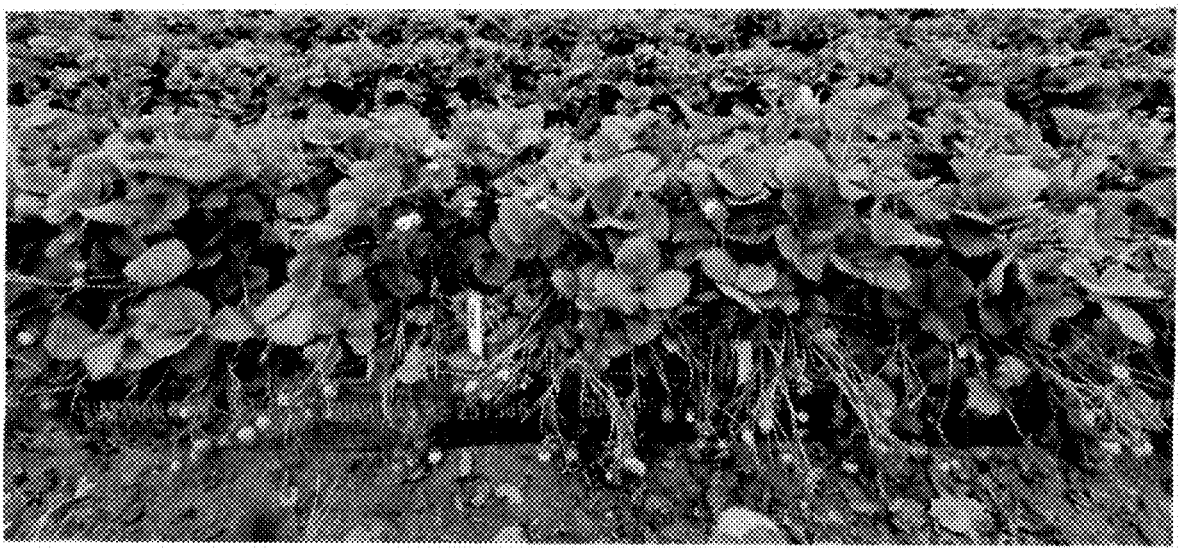
FIG. 7 shows typical plants in a field and the position of ripe fruit on the shoulder.

'GF Belle' is a new and distinct variety of strawberry, known scientifically as *Fragaria* x *ananassa*. It is the result of a cross between its female parent, 'Sweet Ann', and its male parent '001R11'. 'Sweet Ann' is a day neutral variety, while '001R11' is characterized by being a short-day variety. Both parents are remontant in cool coastal environments. 'GF Belle' is a short-day variety that has remontant or ever-bearing tendencies in temperate coastal environments and is partially remontant in warmer inland environments like its parents. Plants of 'GF Belle' bloom only once in our high elevation nursery, and do not bloom in the summer heat of our low elevation nursery location in Manteca, CA, consistent with other short-day varieties. The plants of the new variety have a moderate vigor and produce multiple crowns during the growing season. 'GF Belle' exhibits several characteristics which are improvements over one or both of its parent varieties, and other known cultivars. The characteristics of 'GF Belle' were observed in plants aged about 9 months from planting. These characteristics and comparisons with other cultivars are discussed following.

The fruit size of 'GF Belle' is large, slightly smaller than its 'Sweet Ann' parent, and similar in size, to its other parent '001R11'. The size of fruit of 'GF Belle' is ideal where it is not so large it could be damaged in containers, but not too small to allow for efficient picking and packing. The fruit of 'GF Belle' also hangs down on the shoulder of the bed to allow for highly visible fruit and ease of picking.

'GF Belle' produces mostly conic fruit similar to '001R11', while the fruit of 'Sweet Ann' is mostly long conical. The fruit of 'GF Belle' generally ripens evenly from the tip to the shoulders of the berry, resulting in a uniform light red color over the whole fruit, but has a propensity of developing a seedy tip in certain conditions. In contrast, the fruit of 'Sweet Ann' often has a shoulder that does not ripen all the way to the calyx. The fruit of 'GF Belle' is mostly absent of creases and is generally smooth and has a firmness that is between its two parents, where it is slightly firmer than 'Sweet Ann,' and on par with '001R11'.

The data set forth for 'GF Belle' in Tables 1, 2, and 3 was collected in July 2023 from plants grown at a test plot in Moss Landing, Monterey County, California. Color terminology where noted herein was measured using a handheld Konica Minolta CR-400 colorimeter.

In Table 1, the observed characteristics of 'GF Belle' are set forth.

TABLE 1

| Detailed Description of Characteristics of 'GF Belle' | | |
|---|---|---|
| SPECIFICATION: | | |
| | Genus/ Species | *Fragaria X ananassa* |
| | Market Name | Strawberry |

TABLE 1-continued

| Detailed Description of Characteristics of 'GF Belle' | | |
|---|---|---|
| PARENTS: | | |
| | Female | 'Sweet Ann' (U.S. Plant Pat. No. 22,472) |
| | Male | '001R11' (Unpatented) |
| PLANT: | | |
| | Type | Short Day |
| | Growth Habit | Semi-upright |
| | Foliage density | Moderate |
| | Vigor | Moderate |
| | Height | Average 32.3 cm; range 28.4 cm to 35.8 cm |
| | Width | Average 42.6 cm; range 38.2 cm to 46.1 cm |
| | Crowns | Multiple crowns produced throughout season |
| | Disease tolerance | Moderate susceptibility to Fusarium<br>Moderate susceptibility to Macrophomina<br>Moderate susceptibility to Verticillium wilt |
| LEAF: | | |
| | Width | Average 14.2 cm; range 12.7 cm to 15.3 cm |
| | Color | Adaxial surface: L*, a*, b *: 36.69, −13.89, 20.07<br>Abaxial surface: L*, a*, b *: 53.87, −13.74, 22.74 |
| | Pubescence | Low density |
| | Inter-vein blistering | Slight |
| | Glossiness | Medium |
| | Variegation | None |
| TERMINAL LEAFLET: | | |
| | Length | Average 100.5 mm; range 81.9 mm to 115.1 mm |
| | Width | Average 88.2 mm; range 77.3 mm to 108.1 mm |
| | Ratio Length to width | 1.14 |
| | Margins | Crenate |
| | Leaf shape | Obovate |
| | Base shape | Obtuse |
| | Cross-section shape | Concave |
| PETIOLE: | | |
| | Pubescence | Slight |
| | Petiole color | L*, a*, b *: 54.10, −10.69, 23.19 |
| | Petiole length | Average 29 cm; range 28.2 cm to 30.1 cm |
| | Petiole diameter | Average 4.33 mm; range 3.87 mm to 4.81 mm |
| STIPULE: | | |
| | Anthocyanin coloration | Slight |
| | Length | Average 13.3 mm; range 11.8 mm to 15.1 mm |
| | Width | Average 4.8 mm; range 3.2 mm to 6.4 mm |
| STOLEN: | | |
| | Anthocyanin coloration | Present, slight |
| | Pubescence | Slight, fine |
| | Diameter | Average 3.41 mm; range 3.04 mm to 4.6 mm |
| INFLORESCENCE: | | |
| | Flowering time | Moderately early |
| | Position | Mostly at canopy |
| | Number of blooms | Average 3.9; range 3 to 6 |

TABLE 1-continued

| Detailed Description of Characteristics of 'GF Belle' | | |
|---|---|---|
| | Length | Average 37.2 cm; range 34.2 cm to 43.1 cm |
| | Flower diameter | Average 26.3 mm; range 22.8 mm to 32.3 mm |
| | Petal arrangement | Mostly overlapping |
| | Petal number | Average 6.2; range 5 to 8 |
| | Petal length | Average 12.8 mm; range 9.83 mm to 14.9 mm |
| | Petal width | Average 11.9 mm; range 9.1 mm to 13.9 mm |
| | Ratio Length to width | 1.07 |
| | Petal color | L*, a*, b *: 75.20, −0.93, 10.56 |
| | Calyx | Larger than the corolla |
| | Calyx color (adaxial) | L*, a*, b *: 34.88, −12.31, 15.90 |
| | Calyx color (abaxial) | L*, a*, b *: 50.50, −13.45, 10.31 |
| | Stamens | Average 25.5; range 23 to 28 |
| | Pedicel | Attitude of hairs is upright to perpendicular |
| FRUIT: | | |
| | Bearing | Short day, but remontant in cool coastal climates |
| | Shape | Conic |
| | Size | Seasonal average: 26 g |
| | Achenes | Slightly below fruit surface |
| | Glossiness | Medium |
| | External color | L*, a*, b *: 33.86, 33.08, 19.62 |
| | Internal color | L*, a*, b *: 49.39, 35.64, 35.72 |
| | Evenness of external color | Even |
| | Width of band at top devoid of achenes | Small |
| | Yield | Approximate grams per plant: 540 g |
| | Firmness | Firm, firmer than parent 'Sweet Ann' |
| | % Brix | Average: 7.5; range 6.4 to 8.6 |

Plants and Foliage

The comparison statistics set forth in the following tables are with respect to characteristics observed at mid-season. All measurements for 'GF Belle' were taken at a test plot in Moss Landing, Monterey County, California during 2023. In Tables 2 and 3, the characteristics of 'GF Belle' are compared with historical data of patented varieties 'Ashley Jay' (U.S. Plant Pat. No. 34,637) and 'Miss Jo' (U.S. Plant Pat. No. 34,190.)

The form and structure of the plants of 'GF Belle' are slightly smaller than that of 'Ashley Jay' and 'Miss Jo'. The plant spread of 'GF Belle', is also smaller than that of either 'Miss Jo' or 'Ashley Jay'. The canopy of 'GF Belle' is much more open than that of 'Ashley Jay' and 'Miss Jo'. The leaf surface of 'GF Belle' shows a slight blistering, on par with that of 'Ashley Jay' and 'Miss Jo'. The glossiness of the leaves of 'GF Belle' is glossier than that of 'Ashley Jay' and more closely matched to 'Miss Jo'.

In Table 2, comparative data for foliar characteristics are presented for 'GF Belle' and historical data of two comparison cultivars, 'Ashley Jay' and 'Miss Jo'.

TABLE 2

Foliar Characteristics of 'GF Belle' Compared to 'Miss Jo' and 'Ashley Jay'

| Foliar Characteristics | | Cultivar 'GF Belle' | 'Miss Jo' | 'Ashley Jay' |
|---|---|---|---|---|
| Plant height (mm) | Average | 323 | 360 | 369 |
| | Range | 284-358 | 330-400 | 330-410 |
| Plant spread (mm) | Average | 426 | 542 | 515 |
| | Range | 418-461 | 500-600 | 460-570 |
| Leaf width (mm) | Average | 142 | 156 | 152 |
| | Range | 127-153 | 135-180 | 135-167 |
| Mid-tier leaflet length (mm) | Average | 100.5 | 94.8 | 96 |
| | Range | 81.9-115.1 | 76-108 | 81-115 |
| Mid-tier leaflet width (mm) | Average | 88.2 | 81.6 | 88 |
| | Range | 77.3-108.1 | 69-95 | 69-104 |
| Petiole length (mm) | Average | 290 | 267 | 281 |
| | Range | 282-301 | 232-291 | 250-308 |
| Petiole diameter (mm) | Average | 4.33 | 4.05 | 4.59 |
| | Range | 3.87-4.81 | 3.42-4.81 | 3.72-5.81 |
| Number leaflets per leaf | | 3 | 3 | 3 |
| Leaf convexity | | Concave | Concave | Slight concave |
| Shape leaflet base | | Obtuse | Cuneate | Cuneate |
| Leaf pubescence | | low density | Medium density | Medium density |
| Petiole pubescence | | low density | Low density | Slight |
| Stipule length (mm) | Average | 13.3 | 21.96 | 15.42 |
| | Range | 11.8-15.1 | 19.92-24.58 | 9.7-19.3 |
| Stipule anthocyanin coloration | | Slight | Slight | Slight |
| Leaf margins | | Crenate | Crenate to serrate | Crenate |
| Leaf color adaxial surface (L*, a*, b*) | | 36.69, −13.89, 20.07 | 36.56, −16.09, 23.21 | 32.67, −13.02, 18.02 |
| Leaf color abaxial surface (L*, a*, b*) | | 53.87, −13.74, 22.74 | 50.62, −14.35, 23.04 | 49.88, −13.00, 22.74 |
| Petiole color (L*, a*, b*) | | 54.10, −10.69, 23.19 | 60.04, −14.39, 32.18 | 53.10, −13.59, 31.10 |
| Leaf surface blistering | | Slight | Slight | Slight |
| Leaf surface glossiness | | Moderate | Moderate | Slight |

Flowering and Fruit

'GF Belle' is a short-day variety that has ever-bearing tendencies under certain temperature and horticultural conditions. This has been seen where plants grown in a cool, coastal climate have continuously flowered throughout the growing season, while in nursery production in Manteca where summer temperatures are hot, plants do not flower repeatedly. While 'Miss Jo' has similar inflorescences size to 'GF Belle', 'Ashley Jay' has shorter inflorescences. When compared to their individual plant size, all three varieties produce flowers that are near or above the canopy level, leaving flowers exposed to pollinators, with 'GF Belle' having most flowers exposed. The light red exterior color of the fruit of 'GF Belle' is similar in color to that of 'Ashley Jay' and 'Miss Jo', however 'GF Belle' has a high gloss to it, similar to that of 'Miss Jo'. The fruit of 'GF Belle' has good culinary qualities, including great shape, large size, light red color, and a great strawberry flavor. The fruit storability has not been measured but the fruit retains good physical characteristics and appearance for several days at room temperature and up to a week in common refrigerator conditions of roughly 3° C.

In Table 3, comparative data for flower and fruit characteristics for 'Ashley Jay', 'Miss 9 Jo', and 'GF Belle', are set forth.

TABLE 3

Flower and Fruit Characteristics of 'GF Belle' Compared to 'Miss Jo' and 'Ashley Jay'

| Characteristic | | Cultivar 'GF Belle' | 'Miss Jo' | 'Ashley Jay' |
|---|---|---|---|---|
| Petal number | | 5-8 | 5-8 | 5-8 |
| Petal length (mm) | Average | 12.8 | 11.37 | 12.39 |
| | Range | 9.83-14.9 | 10.16-12.51 | 9.74-15.28 |
| Petal width (mm) | Average | 11.9 | 10.84 | 12.27 |
| | Range | 9.1-13.9 | 9.23-12.15 | 9.24-14.93 |
| Position of flower (relative to foliage) | | most exposed | most exposed some even | most even |
| Pedicel length (mm) | Average | 372 | 372 | 336 |
| | Range | 342-431 | 329-435 | 270-422 |
| Sepal color (adaxial) | (L*, a*, b*) | 34.88, −12.31, 15.90 | 34.17, −11.73, 15.65 | 31.55, −10.36, 13.26 |
| Sepal color (abaxial) | (L*, a*, b*) | 50.50, −13.45, 10.31 | 46.92, −13.25, 21.97 | 43.01, −14.20, 21.77 |
| Flower diameter (mm) | Average | 28.18 | 26.55 | 25.8 |
| | Range | 23.5-34.2 | 21.86-30.22 | 22.4-29.1 |
| Fruit color (external) | (L*, a*, b*) | 33.86, 33.08, 19.62 | 39.79, 37.51, 29.62 | 40.99, 41.96, 29.56 |
| Fruit color (internal) | (L*, a*, b*) | 49.39, 35.64, 35.72 | 43.88, 39.08, 37.72 | 54.75, 34.16, 37.50 |

Leaf samples from 'GF Belle', along with several proprietary selections from the breeding program were submitted to a lab for allelic fingerprint comparison to the over two hundred other varieties of strawberry in its database. The allelic fingerprint analysis establishes that 'GF Belle' is distinct and unique compared to the lab's large database of allelic fingerprints. Table 4 below sets forth the test results for a selection of varieties in comparison to 'GF Belle': 'Ashley Jay' (U.S. Plant Pat. No. 34,637), 'Camila' (U.S. Plant Pat. No. 30,326), 'Emilia' (U.S. Plant Pat. No. 30,427), 'Lucia' (U.S. Plant Pat. No. 26,974), 'Miss Jo' (U.S. Plant Pat. No. 34,190), 'Ruby June' (U.S. Plant Pat. No. 27,190), 'Sangria' (U.S. Plant Pat. No. 30,426), 'Scarlet' (U.S. Plant Pat. No. 27,034), 'Sierra' (U.S. Plant Pat. No. 33,284), and 'Sweet Ann' (U.S. Plant Pat. No. 22,472).

TABLE 4

Allelic Fingerprint Analysis

| Cultivar | M1 | M2 | M3 |
|---|---|---|---|
| 'Ashley Jay' | 206, 224, 229 | 188, 216, 232 | 279, 281, 289 |
| 'Camila' | 204, 206, 224, 229 | 190, 232 | 279, 281, 289 |
| 'Emilia' | 204, 206, 214, 229 | 190, 232 | 279, 281, 289 |
| 'Lucia' | 202, 204, 206, 229 | 188, 216, 232 | 279, 281, 289 |
| 'Miss Jo' | 204, 206, 214, 224, 229 | 190, 232, 263 | 279, 281, 289 |

TABLE 4-continued

| Allelic Fingerprint Analysis | | | |
|---|---|---|---|
| Cultivar | M1 | M2 | M3 |
| 'Ruby June' | 206, 224, 229 | 188, 190, 216, 232 | 279, 289 |
| 'Sangria' | 204, 206, 229 | 190, 216 | 279, 289 |
| 'Scarlet' | 204, 206, 214, 229 | 173, 190, 232 | 279, 281, 289 |
| 'Sierra' | 204, 206, 229 | 232 | 279, 289 |
| 'Sweet Ann' | 204, 206, 229 | 190, 216, 232 | 279, 281, 289 |
| 'GF Belle' | 204, 206, 222, 224, 229 | 188, 216, 232 | 279, 281,289 |

We claim:

1. A new and distinct strawberry plant named 'GF Belle' as described and illustrated herein.

* * * * *